US008080672B2

(12) United States Patent
Pinchasov et al.

(10) Patent No.: US 8,080,672 B2
(45) Date of Patent: Dec. 20, 2011

(54) CRYSTAL FORM OF ATORVASTATIN HEMI-CALCIUM AND PROCESSES FOR PREPARATION THEREOF

(75) Inventors: Michael Pinchasov, Dover, NJ (US); Judith Aronhime, Rehovot (IL); Zvika Doani, Tel-Mond (IL)

(73) Assignee: Teva Pharmaceutical Industries Ltd., Petach Tikva (IL)

( * ) Notice: Subject to any disclaimer, the term of this patent is extended or adjusted under 35 U.S.C. 154(b) by 824 days.

(21) Appl. No.: 11/638,832

(22) Filed: Dec. 13, 2006

(65) Prior Publication Data
US 2007/0232683 A1    Oct. 4, 2007

Related U.S. Application Data (60) Provisional application No. 60/749,603, filed on Dec. 13, 2005.

(51) Int. Cl.
C07D 207/32 (2006.01)
A61K 31/402 (2006.01)

(52) U.S. Cl. ........................ 548/537; 514/423
(58) Field of Classification Search .................. 548/537; 514/423
See application file for complete search history.

(56) References Cited

U.S. PATENT DOCUMENTS

| 4,681,893 | A | 7/1987 | Roth |
| 5,003,080 | A | 3/1991 | Butler et al. |
| 5,097,045 | A | 3/1992 | Butler et al. |
| 5,124,482 | A | 6/1992 | Butler et al. |
| 5,149,837 | A | 9/1992 | Butler et al. |
| 5,216,174 | A | 6/1993 | Butler et al. |
| 5,245,047 | A | 9/1993 | Butler et al. |
| 5,273,995 | A | 12/1993 | Roth |
| 5,280,126 | A | 1/1994 | Butler et al. |
| 5,298,627 | A | 3/1994 | Butler et al. |
| 5,385,929 | A | 1/1995 | Bjorge et al. |
| 5,959,156 | A | 9/1999 | Hagen et al. |
| 5,969,156 | A | 10/1999 | Briggs et al. |
| 6,121,461 | A | 9/2000 | McKenzie |
| 6,600,051 | B2 | 7/2003 | Tully |
| 6,605,636 | B2 | 8/2003 | Aronhime et al. |
| 6,605,729 | B1 | 8/2003 | Byrn et al. |
| 6,992,194 | B2 | 1/2006 | Lidor-Hadas et al. |
| 7,074,818 | B2 | 7/2006 | Manne et al. |
| 7,144,915 | B2 | 12/2006 | Byrn et al. |
| 7,144,916 | B2 | 12/2006 | Aronhime et al. |
| 7,151,183 | B2 | 12/2006 | Tessler et al. |
| 7,411,075 | B1 | 8/2008 | Ayalon et al. |
| 2002/0099224 | A1 | 7/2002 | Niddam et al. |
| 2002/0115709 | A1 | 8/2002 | Aronhime et al. |
| 2002/0183378 | A1 | 12/2002 | Aronhime et al. |
| 2003/0114686 | A1 | 6/2003 | Van Der Schaaf et al. |
| 2003/0212279 | A1 | 11/2003 | Tessler et al. |
| 2003/0216584 | A1 | 11/2003 | Aronhime et al. |
| 2004/0054193 | A1 | 3/2004 | Byrn et al. |
| 2004/0106670 | A1 | 6/2004 | Blatter et al. |
| 2004/0220255 | A1* | 11/2004 | Schaaf et al. .................. 514/423 |
| 2004/0242899 | A1 | 12/2004 | Reddy et al. |
| 2005/0004206 | A1 | 1/2005 | Aronhime et al. |
| 2005/0090542 | A1 | 4/2005 | Aronhime et al. |
| 2005/0209306 | A1 | 9/2005 | Jegorov et al. |
| 2005/0282885 | A1 | 12/2005 | Tessler et al. |
| 2006/0020137 | A1 | 1/2006 | Tessler et al. |
| 2006/0063826 | A1 | 3/2006 | Lifshitz-Liron et al. |
| 2006/0100446 | A1 | 5/2006 | Aronhime et al. |
| 2006/0106231 | A1 | 5/2006 | Aronhime et al. |
| 2006/0122403 | A1 | 6/2006 | Suri et al. |
| 2006/0205805 | A1 | 9/2006 | Van Der Schaaf et al. |
| 2006/0241169 | A1 | 10/2006 | Park |
| 2007/0032665 | A1 | 2/2007 | Gudipati et al. |
| 2008/0306282 | A1 | 12/2008 | Krzyzaniak et al. |

FOREIGN PATENT DOCUMENTS

| CA | 2521776 | 1/2003 |
| EP | 0848704 | 6/1998 |
| EP | 0848705 | 6/1998 |
| EP | 1148049 | 10/2001 |
| EP | 1235799 | 9/2002 |
| EP | 1424324 | 6/2004 |
| EP | 1783113 | 5/2007 |
| WO | WO97/03958 | 2/1997 |
| WO | WO 97/03959 | 2/1997 |
| WO | WO 01/36384 | 5/2001 |
| WO | WO 02/41834 | 5/2002 |
| WO | WO 02/43732 | 6/2002 |
| WO | WO02/051804 | 7/2002 |
| WO | WO02/057229 | 7/2002 |
| WO | WO 03/004470 | 1/2003 |
| WO | WO 03/011826 | 2/2003 |
| WO | WO03/050085 | 6/2003 |
| WO | WO 03/070702 | 8/2003 |
| WO | WO03/082816 | 10/2003 |
| WO | WO2004/022053 | 3/2004 |
| WO | WO2004/043918 | 5/2004 |
| WO | WO2004/050618 | 6/2004 |
| WO | WO2005/026116 | 3/2005 |
| WO | WO2005/090301 | 9/2005 |
| WO | WO2005/105738 | 11/2005 |

(Continued)

OTHER PUBLICATIONS

US Pharmacopia #23, national formulary #18.*
Morissette et al. Advanced Drug Delivery Reviews 56 (2004) 275-300.*
Byrn et al., Pharm. Res., (1995) v. 12, n. 7, p. 945-54.*
Brittain (Polymorphism in Pharmaceutical Solids, vol. 95, 1999, Taylor & Francis, Harry G. Brittain (Ed.), 427 pp.).*
Tiwari et al., J. Pharm. Biomed. Anal., 43 (2007) 865-72.*
Campbell Roberts et al., J. Pharm. Biomed. Anal., 28 (2002) 1149-59.*
Hurst et al., Analytica Chimica Acta, 337 (1997), 233-52.*
Baumann, K.L. et al., *Tetrahydron Letters*, 1992, 33, 2283-2284.
Caira, M.R., "Crystalline Polymorphism of Organic Compounds," *Topics in Current Chemistry*, (1998) vol. 198, pp. 163-208, Springer, Berlin, DE.

(Continued)

*Primary Examiner* — Robert Havlin
(74) *Attorney, Agent, or Firm* — Kenyon & Kenyon LLP (57) ABSTRACT

Provided is a crystal form of atorvastatin hemi-calcium and processes for its preparation.

15 Claims, 11 Drawing Sheets

FOREIGN PATENT DOCUMENTS

| WO | WO2006/011041  | 2/2006  |
|----|----------------|---------|
| WO | WO2006/045865  | 5/2006  |
| WO | WO 2006/048894 | 5/2006  |
| WO | WO2006/106372  | 10/2006 |
| WO | WO2007/070667  | 6/2007  |
| WO | WO2007/096903  | 8/2007  |
| WO | WO2007/133597  | 11/2007 |
| WO | WO2008/002655  | 1/2008  |

OTHER PUBLICATIONS

Lipid Research Clinics Program, "The Lipid Research Clinics Coronary Primary Prevention Trial Results: I. Reduction in Incidence of Coronary Heart Disease", *J.A.M.A.*, 1984, 351-74, vol. 251, No. 3.

Scandinavian Simvastatin Survival Study Group, "Randomised Trial of Cholesterol Lowering in 4444 Patients With Coronary Heart Disease: The Scandinavian Survival Study (4s)", *The Lancet*, 1994, pp. 1383-1389, vol. 344.

Witztum, "Chapter 36: Drugs Used in the Treatment of Hyperlipoproteinemias", *Goodman & Gilman's The Pharmacological Basis of Therapeutics, $9^{th}$ ed.*, 1996, pp. 875-897.

International Search Report from PCT/US2006/047834, dated Jun. 1, 2007.

Caira, Mino R., "Crystalline Polymorphism of Organic Compounds," Topics in Current Chemistry, 1998, vol. 198, pp. 163-208.

Llinàs, Antonio, and Goodman, Jonathan M., "Polymorph Control: Past, Present and Future," Drug Discovery Today, Mar. 2008, vol. 13 (Nos. 5/6), pp. 198-210.

Japanese Office Action, dated Nov. 30, 2010, from corresponding Japanese Patent Application No. 2007-555403 and English-language translation thereof.

Taiwanese Office Action, dated Nov. 23, 2010, from corresponding Taiwanese Patent Application No. 095146783 and English-language translation thereof.

\* cited by examiner

CRYSTAL FORM OF ATORVASTATIN HEMI-CALCIUM AND PROCESSES FOR PREPARATION THEREOF

RELATED APPLICATIONS

This application claims the benefit of priority to U.S. Provisional Application No. 60/749,603, filed Dec. 13, 2005, the contents of which are incorporated herein by reference.

FIELD OF THE INVENTION

The present invention relates to a novel crystalline polymorphic form of atorvastatin hemi-calcium, novel processes for preparing said crystalline form and pharmaceutical compositions comprising said crystalline form.

BACKGROUND OF THE INVENTION

Atorvastatin, ([R—(R*,R*)]-2-(4-fluorophenyl)-P,6-dihydroxy-5-(1-methylethyl)-3-phenyl-4-[(phenylamino)carbonyl]-1H-pyrrole-1-heptanoic acid), depicted in lactone form in formula (I) and its calcium salt of formula (II) are well known in the art, and described inter alia, in U.S. Pat. Nos. 4,681,893, and 5,273,995, which are herein incorporated by reference.

Formula I

Formula II

Processes for preparing atorvastatin and its hemi-calcium salt are also disclosed in U.S. Patent Application Publication No. 2002/0099224; U.S. Pat. Nos. 5,273,995; 5,298,627; 5,003,080; 5,097,045; 5,124,482; 5,149,837; 5,216,174; 5,245,047; and 5,280,126; and Baumann, K. L. et al. Tet. Lett. 1992, 33, 2283-2284, which are hereby incorporated by reference.

Atorvastatin is a member of the class of drugs called statins. Statin drugs are currently the most therapeutically effective drugs available for reducing low density lipoprotein (LDL) particle concentration in the blood stream of patients at risk for cardiovascular disease. A high level of LDL in the bloodstream has been linked to the formation of coronary lesions which obstruct the flow of blood and can rupture and promote thrombosis. Goodman and Gilman, *The Pharmacological Basis of Therapeutics* 879 (9th ed., 1996). Reducing plasma LDL levels has been shown to reduce the risk of clinical events in patients with cardiovascular disease and patients who are free of cardiovascular disease but who have hypercholesterolemia. Scandinavian Simvastatin Survival Study Group, 1994; Lipid Research Clinics Program, 1984a, 1984b.

The believed mechanism of action of statin drugs has been elucidated in some detail. Specifically, it is believed that statins interfere with the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion of HMG to mevalonate, which is the rate determining step in the biosynthesis of cholesterol, and so its inhibition leads to a reduction in the concentration of cholesterol in the liver. Very low density lipoprotein (VLDL) is the biological vehicle for transporting cholesterol and triglycerides from the liver to peripheral cells. VLDL is catabolized in the peripheral cells which releases fatty acids which may be stored in adipocytes or oxidized by muscle. The VLDL is converted to intermediate density lipoprotein (IDL), which is either removed by an LDL receptor, or is converted to LDL. Decreased production of cholesterol leads to an increase in the number of LDL receptors and corresponding reduction in the production of LDL particles by metabolism of IDL.

Atorvastatin hemi-calcium salt trihydrate is marketed under the name LIPITOR® by Pfizer, Inc. Atorvastatin is disclosed in U.S. Pat. No. 4,681,893 and the hemi-calcium salt depicted in formula (II) above is disclosed in U.S. Pat. No. 5,273,995. The '995 patent teaches that the hemi-calcium salt is obtained by crystallization from a brine solution resulting from the transposition of the sodium salt with $CaCl_2$ and further purified by recrystallization from a 5:3 mixture of ethyl acetate and hexane.

The occurrence of different crystal forms (polymorphism) is a property of some molecules and molecular complexes. A single molecule, like the atorvastatin in formula (I) or the salt complex of formula (II), may give rise to a variety of solids having distinct physical properties like melting point, X-ray diffraction pattern, infrared absorption fingerprint and NMR spectrum. The differences in the physical properties of polymorphs is believed to result from the orientation and intermolecular interactions of adjacent molecules (complexes) in the bulk solid. Accordingly, polymorphs are seen as distinct solids sharing the same molecular formula but having distinct physical properties compared to other forms in the polymorph family.

One of the most important physical properties of pharmaceutical polymorphs is their solubility in aqueous solution, particularly their solubility in the gastric juices of a patient. For example, where absorption through the gastrointestinal tract is slow, it is often desirable for a drug that is unstable in the patient's stomach or intestine to dissolve slowly so that it does not accumulate in a deleterious environment. On the other hand, where the effectiveness of a drug correlates with peak bloodstream levels of the drug, a property shared by statin drugs, provided the drug is rapidly absorbed by the GI system, a more rapidly dissolving form is likely to exhibit increased effectiveness over a comparable amount of a more slowly dissolving form.

Crystalline Forms I, II, III and IV of atorvastatin hemi-calcium are the subjects of U.S. Pat. Nos. 5,959,156 and 6,121,461. Crystalline atorvastatin hemi-calcium Form V is disclosed in International Publication No. WO 01/36384. Other crystalline forms of atorvastatin hemi-calcium are disclosed in International Publication Nos. WO 02/43732, WO 02/41834 and WO 03/070702.

The discovery of new crystalline polymorphic forms of a drug enlarges the repertoire of materials that a formulation scientist has with which to design a pharmaceutical dosage form of a drug with a targeted release profile or other desired characteristic. Thus, it is advantageous to develop new crystalline polymorphic forms of drugs.

SUMMARY OF THE INVENTION

In one embodiment, the invention relates to a crystalline atorvastatin hemi-calcium characterized by a powder XRD pattern with most intense peaks at 2.9, 8.25, 8.95, 18.4±0.25 degrees 2θ.

In another embodiment, the invention relates to a process for preparing the above crystalline atorvastatin hemi-calcium comprising:

slurrying atorvastatin hemi-calcium Form V in a mixture comprising ethanol and water to obtain crystalline atorvastatin hemi-calcium characterized by a powder XRD pattern with most intense peaks at 2.9, 8.25, 8.95, 18.4±0.25 degrees 2θ.

In yet another embodiment, the invention relates to a pharmaceutical composition comprising crystalline atorvastatin hemi-calcium characterized by a powder XRD pattern with most intense peaks at 2.9, 8.25, 8.95, 18.4±0.25 degrees 2θ and at least one pharmaceutically acceptable excipient.

DETAILED DESCRIPTION OF THE INVENTION

The present invention provides a solid crystalline atorvastatin hemi-calcium. This crystalline form can be produced on an industrial scale with a slurry process. It is designated herein as Form T1.

Figure 1:
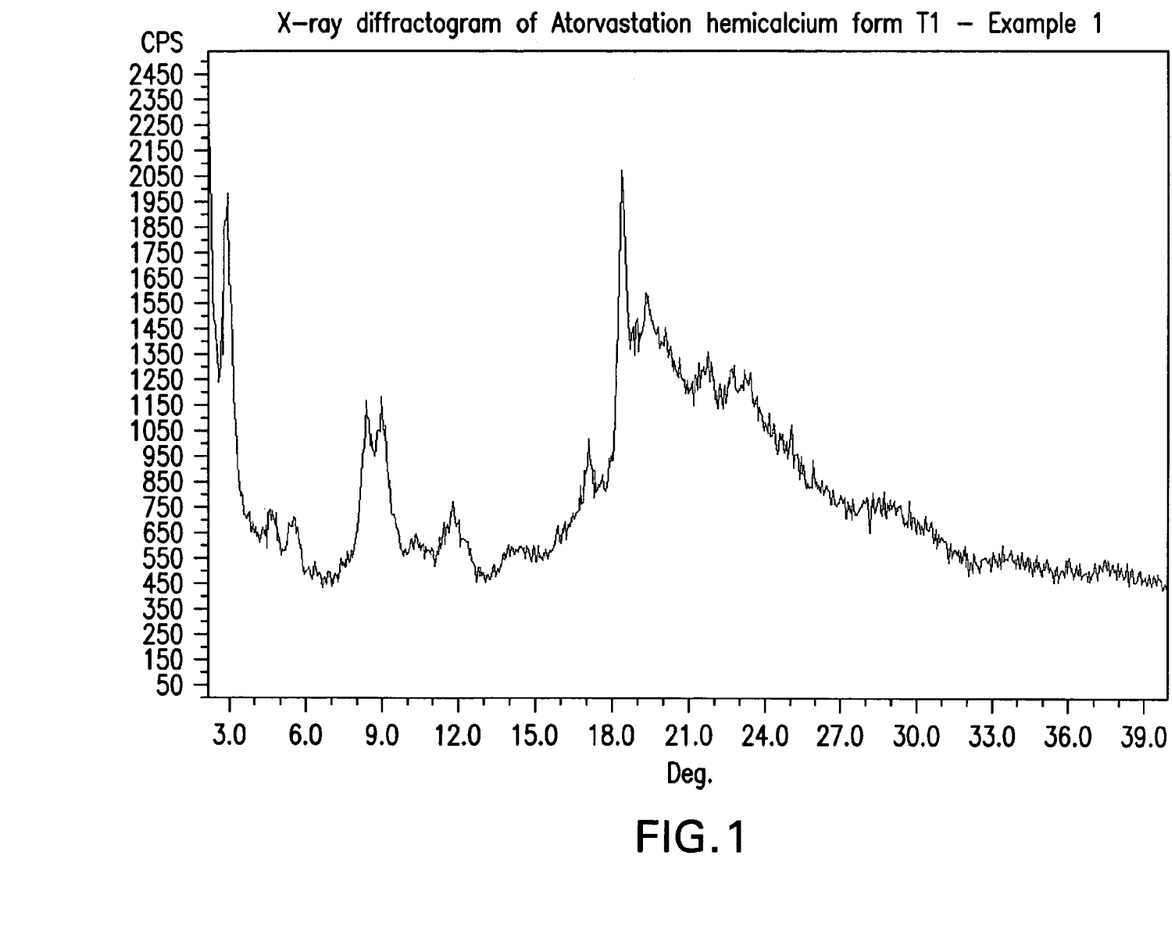
FIG. 1 is an X-ray diffractogram of a sample of atorvastatin hemicalcium form T1 obtained from Example 1.
Figure 2:
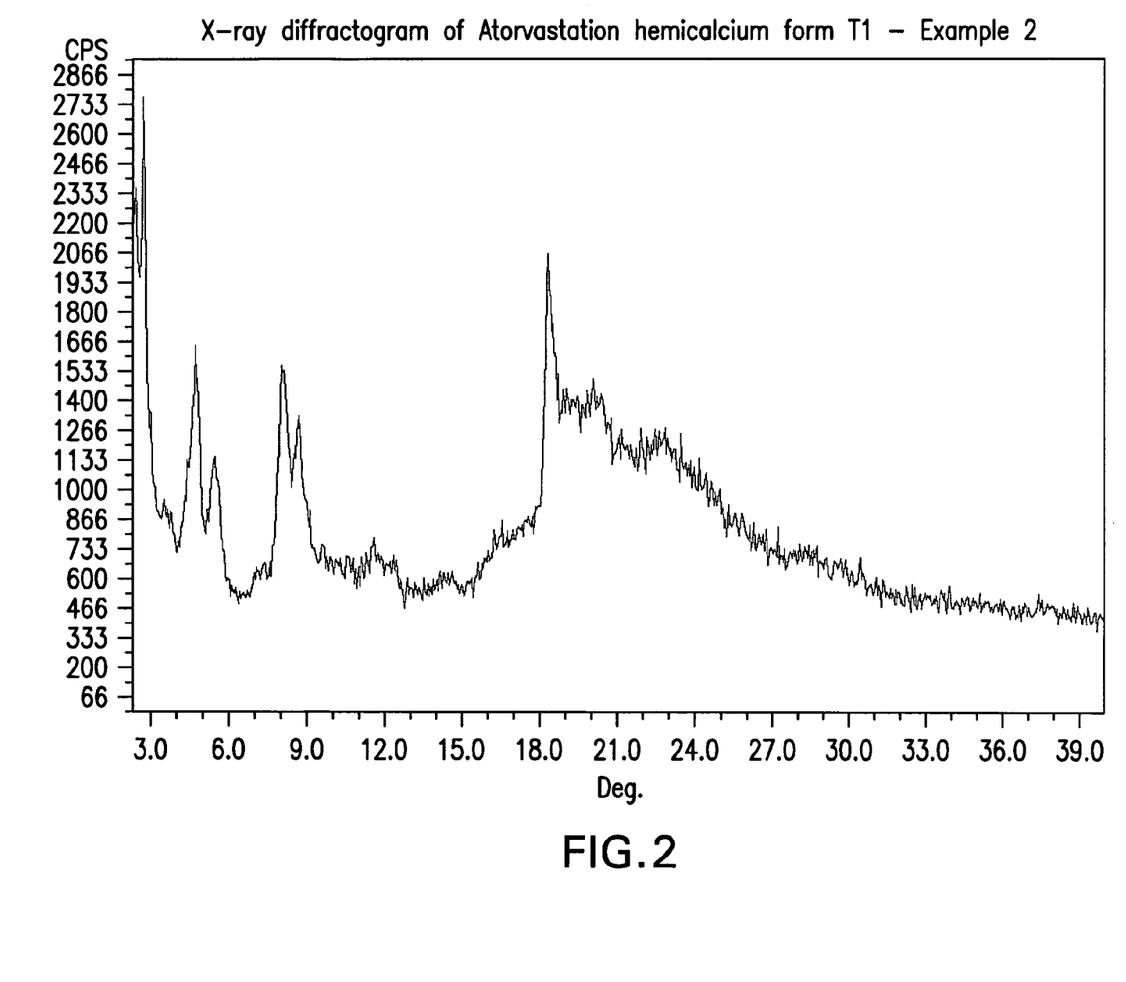
FIG. 2 is an X-ray diffractogram of a sample of Atorvastatin hemicalcium form T1 obtained from Example 2.
Figure 3:
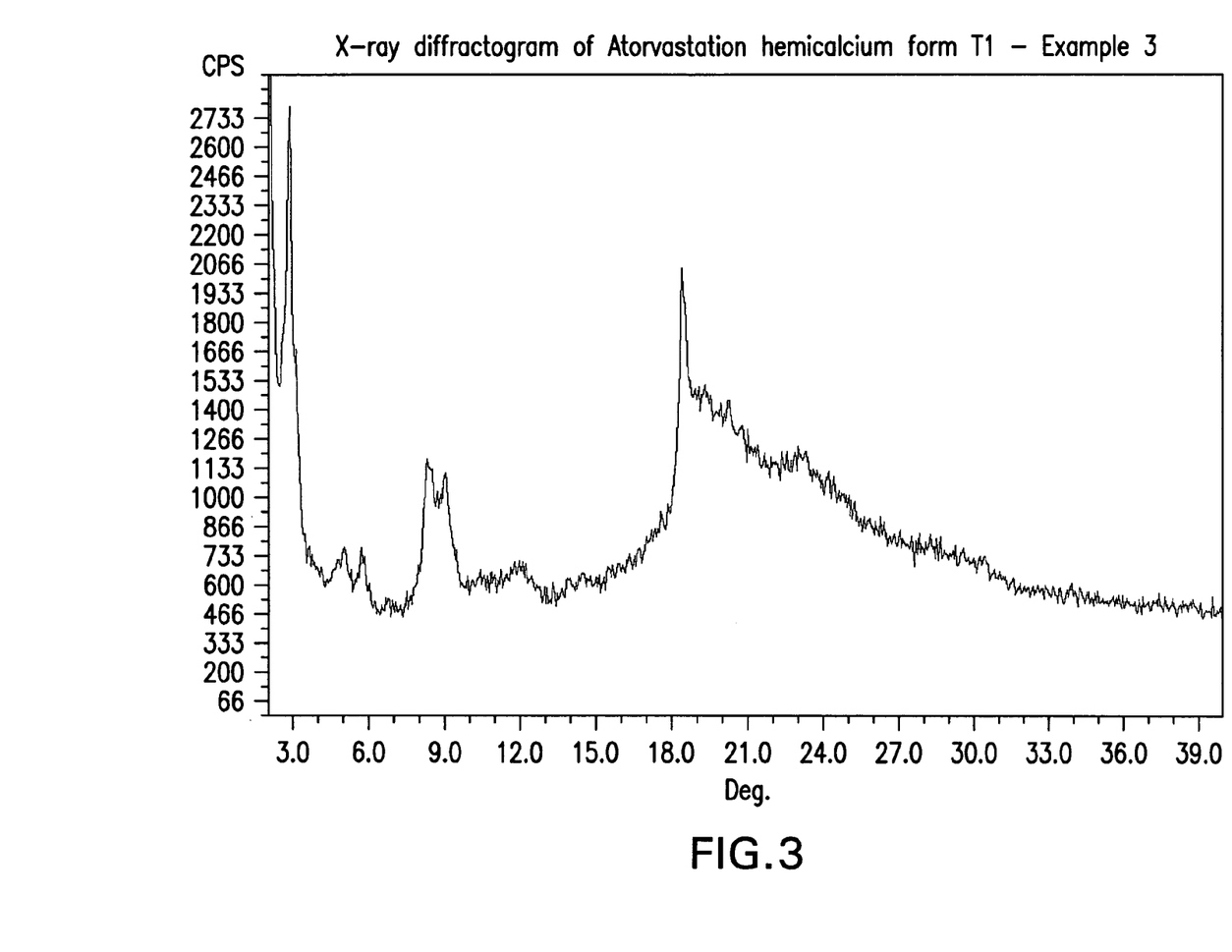
FIG. 3 is an X-ray diffractogram of a sample of Atorvastatin hemicalcium form T1 obtained from Example 3.
Figure 4:
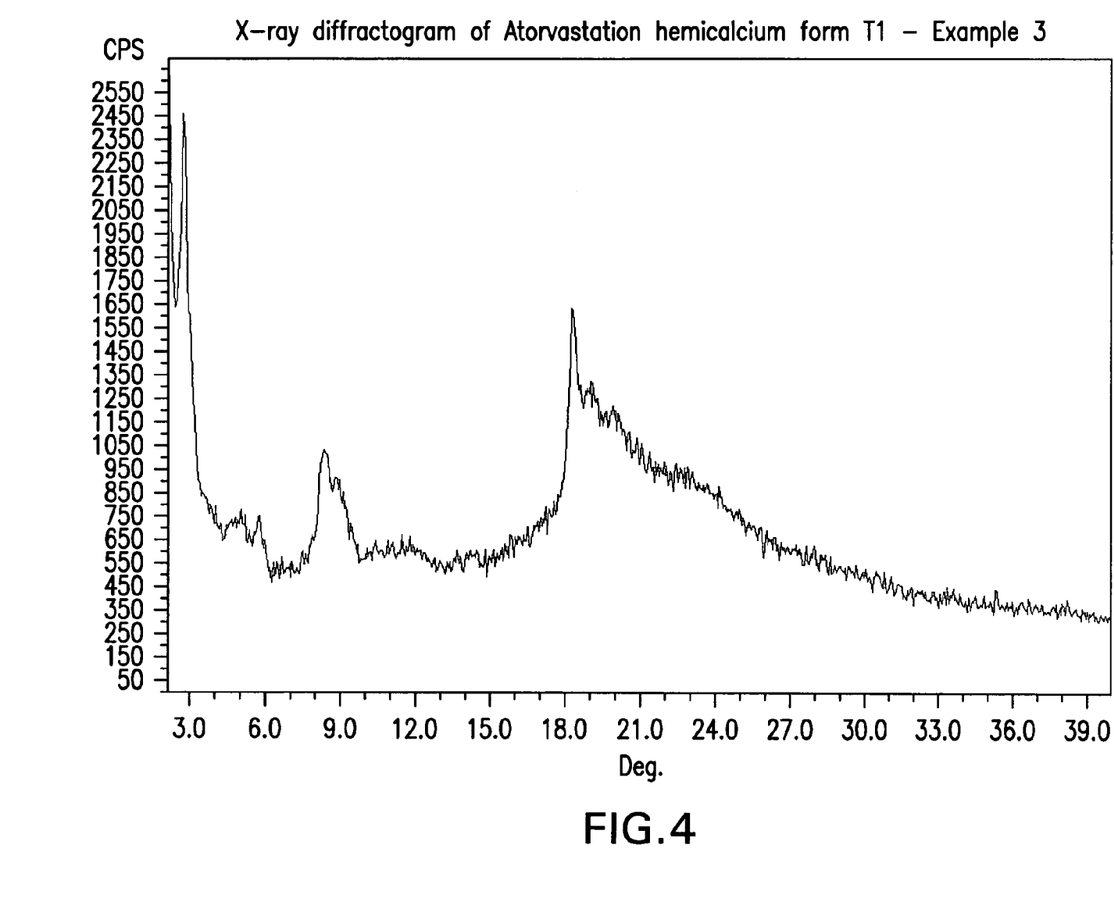
FIG. 4 is an X-ray diffractogram of a sample of Atorvastatin hemicalcium form T1 obtained from Example 3.
Figure 5:
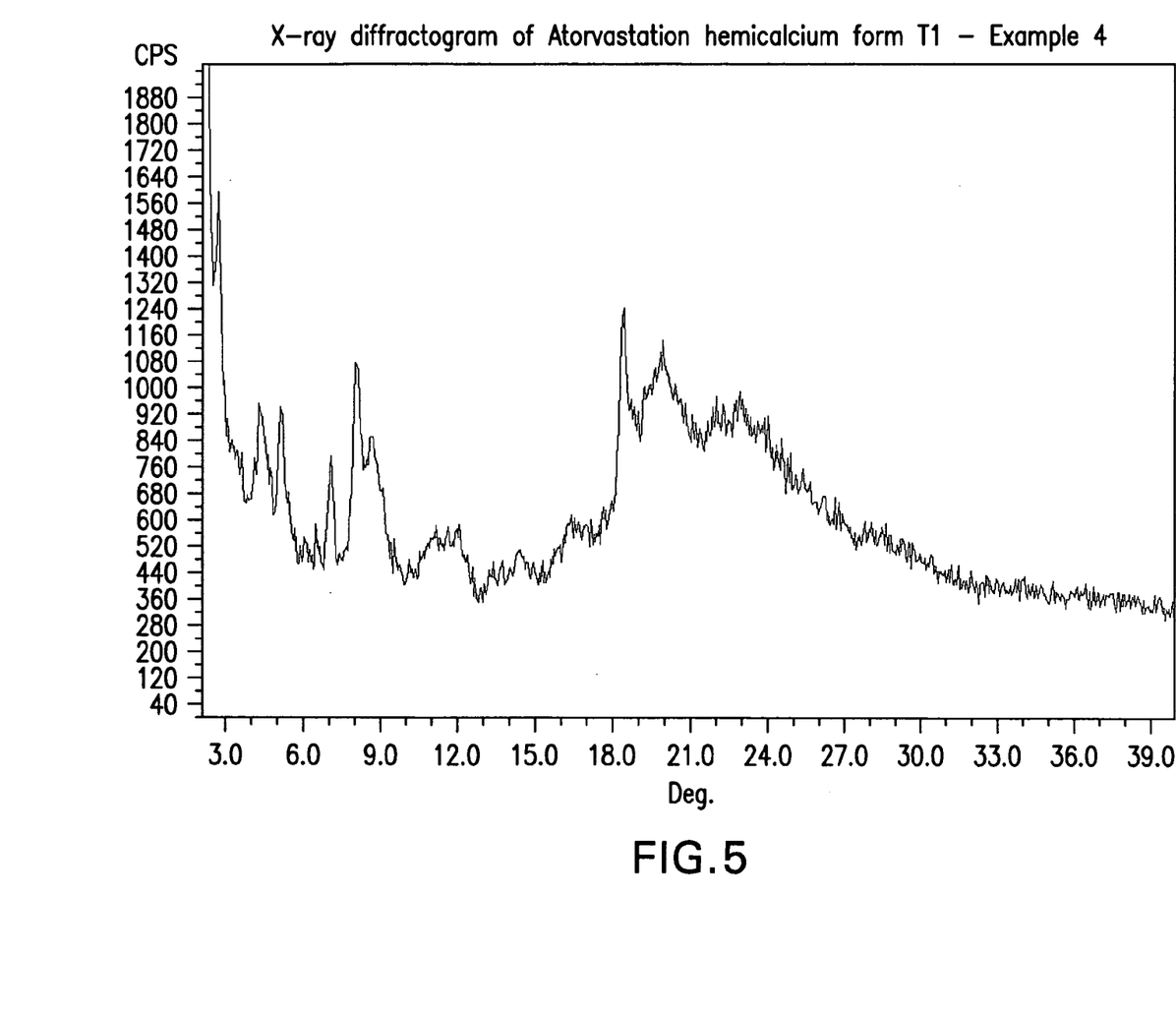
FIG. 5 is an X-ray diffractogram of a sample of Atorvastatin hemicalcium form T1 obtained from Example 4.
Figure 6:
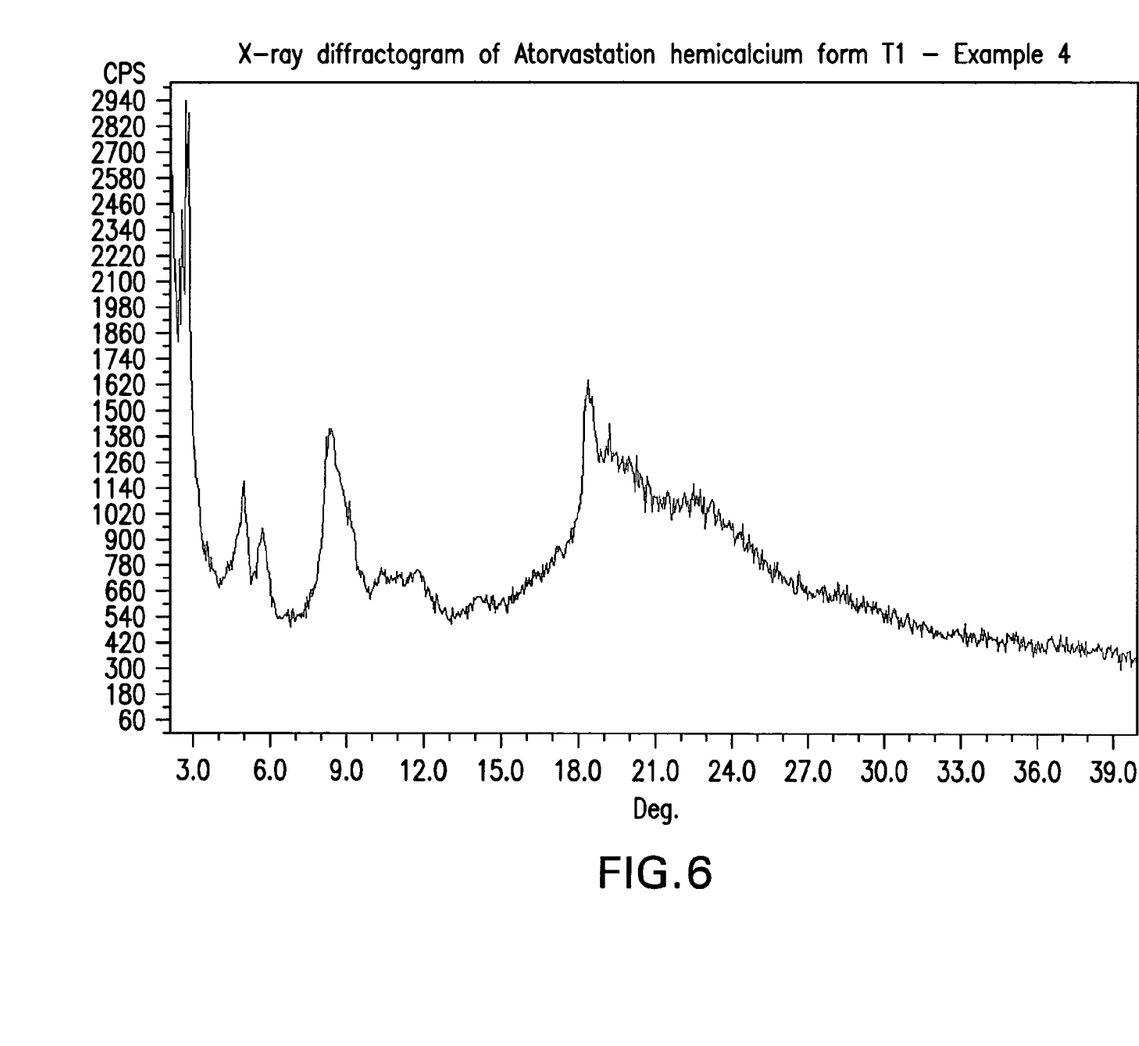
FIG. 6 is an X-ray diffractogram of a sample of Atorvastatin hemicalcium form T1 obtained from Example 4.
Figure 7:
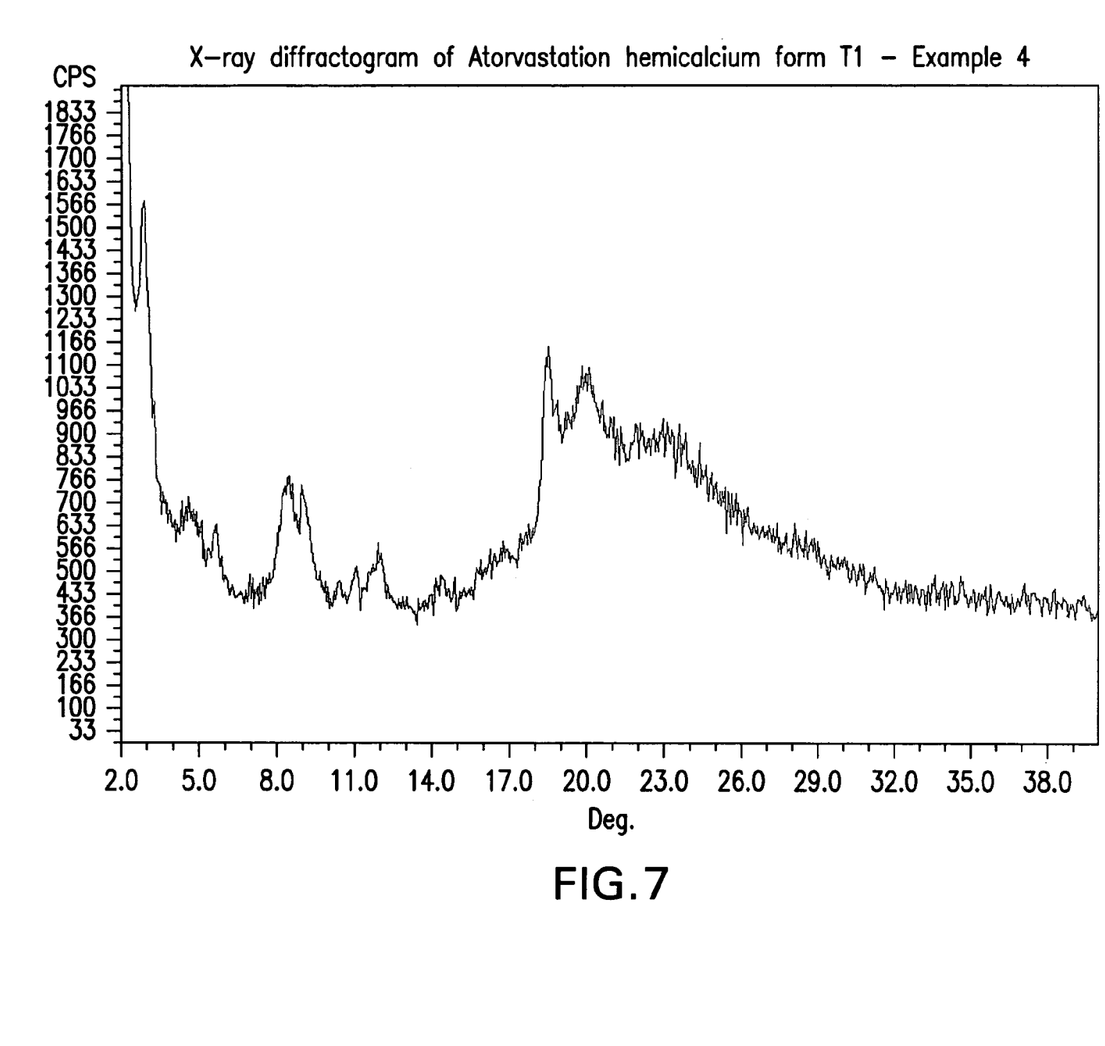
FIG. 7 is an X-ray diffractogram of a sample of Atorvastatin hemicalcium form T1 obtained from Example 4.
Figure 8:
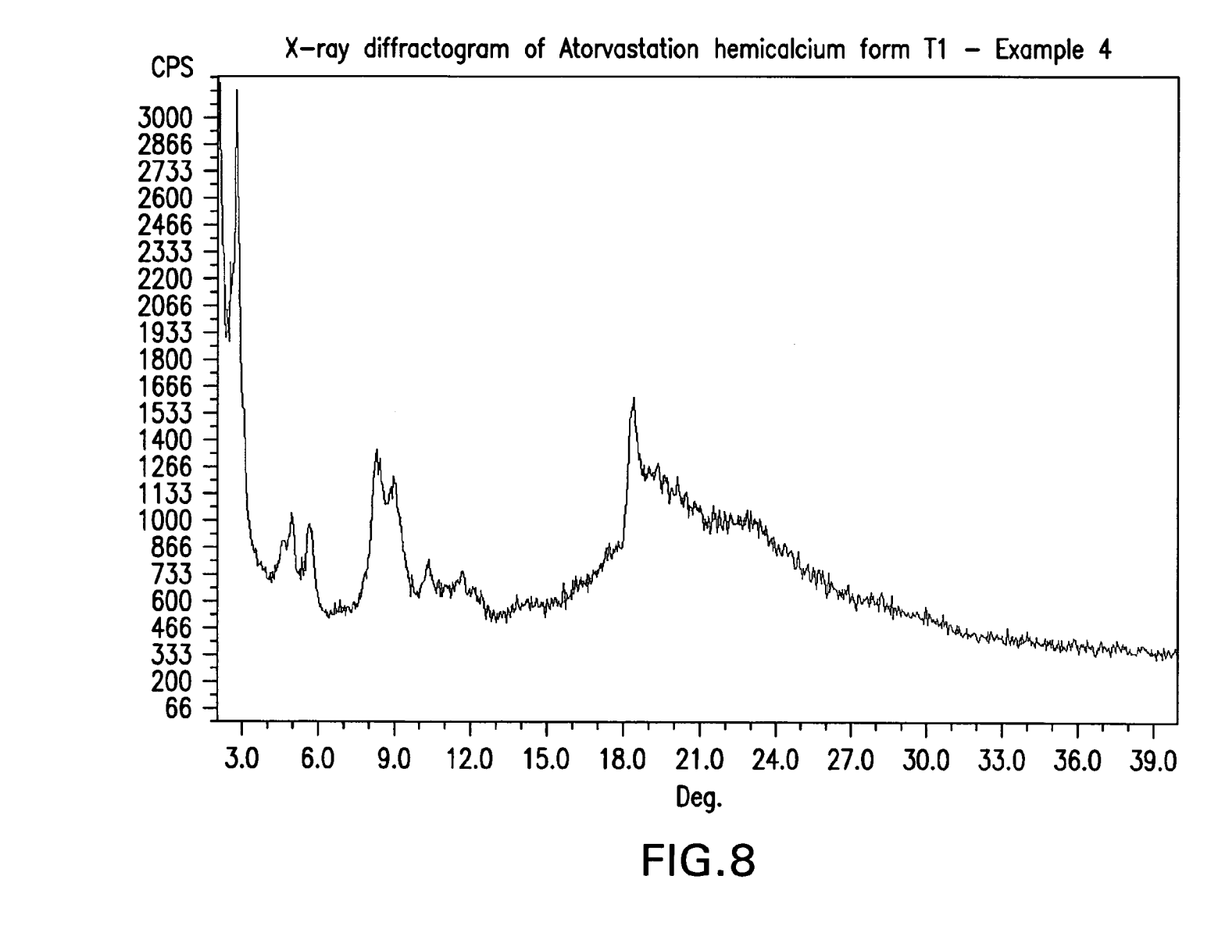
FIG. 8 is an X-ray diffractogram of a sample of Atorvastatin hemicalcium form T1 obtained from Example 4.
Figure 9:
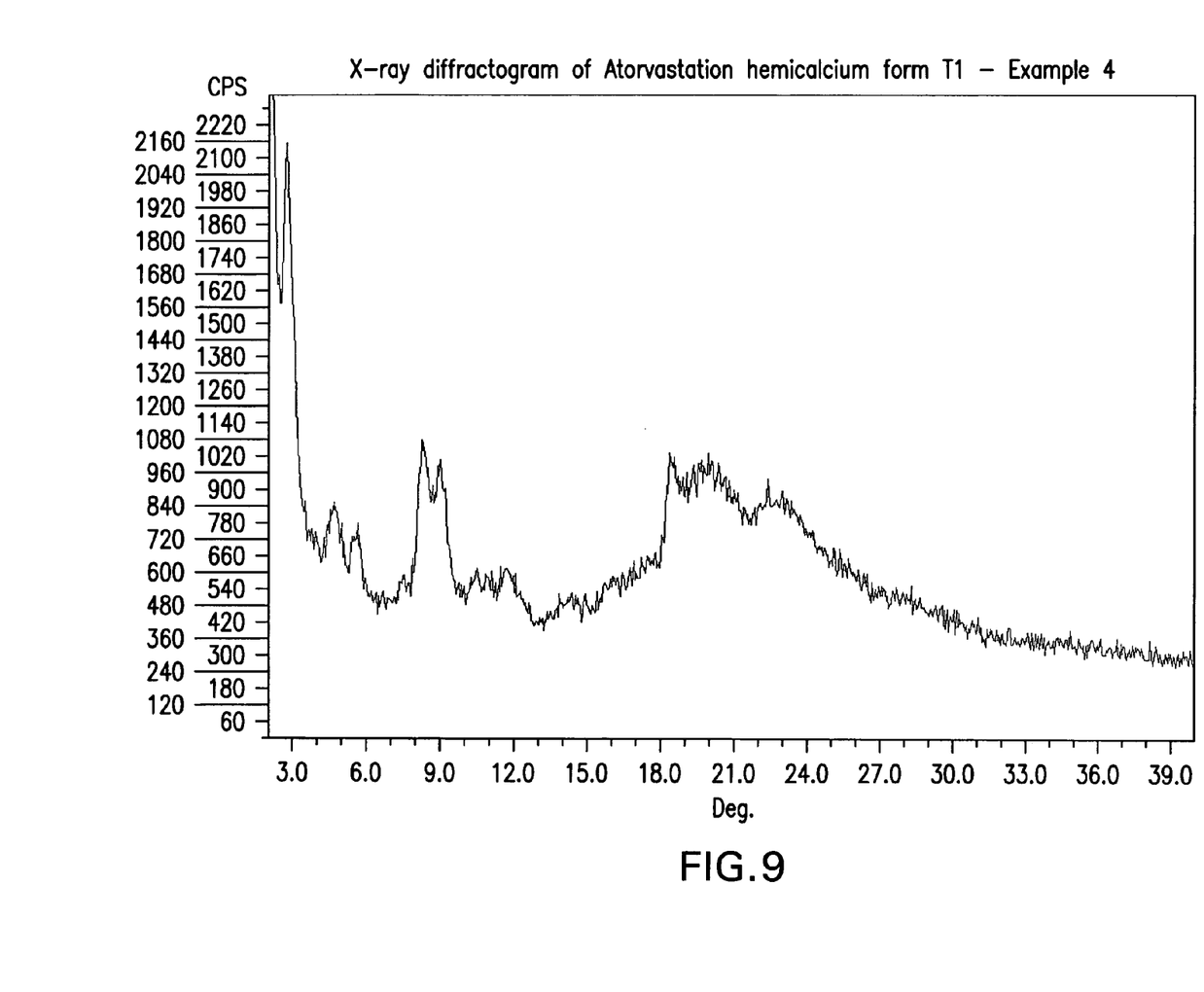
FIG. 9 is an X-ray diffractogram of a sample of Atorvastatin hemicalcium form T1 obtained from Example 4.
Figure 10:
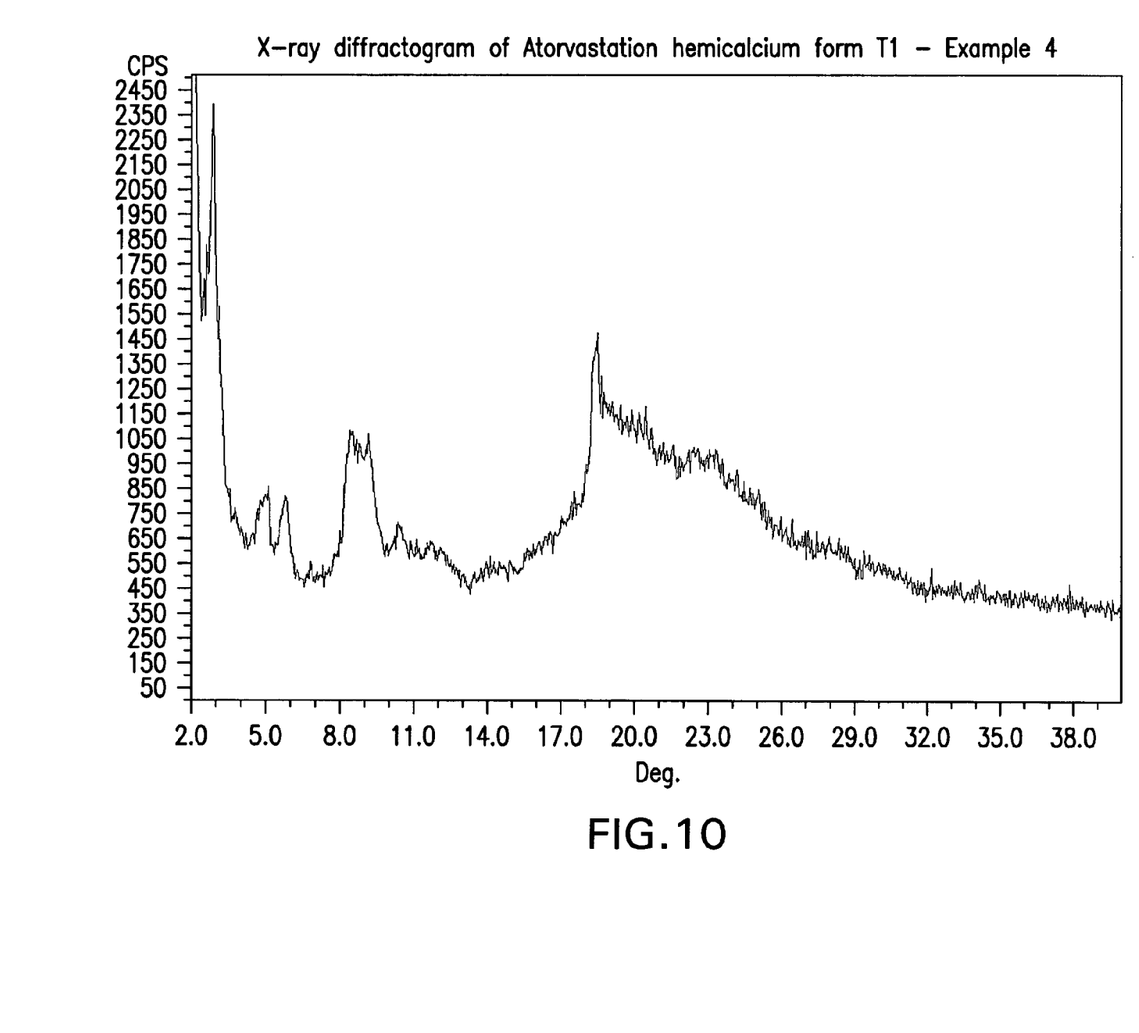
FIG. 10 is an X-ray diffractogram of a sample of Atorvastatin hemicalcium form T1 obtained from Example 4.
Figure 11:
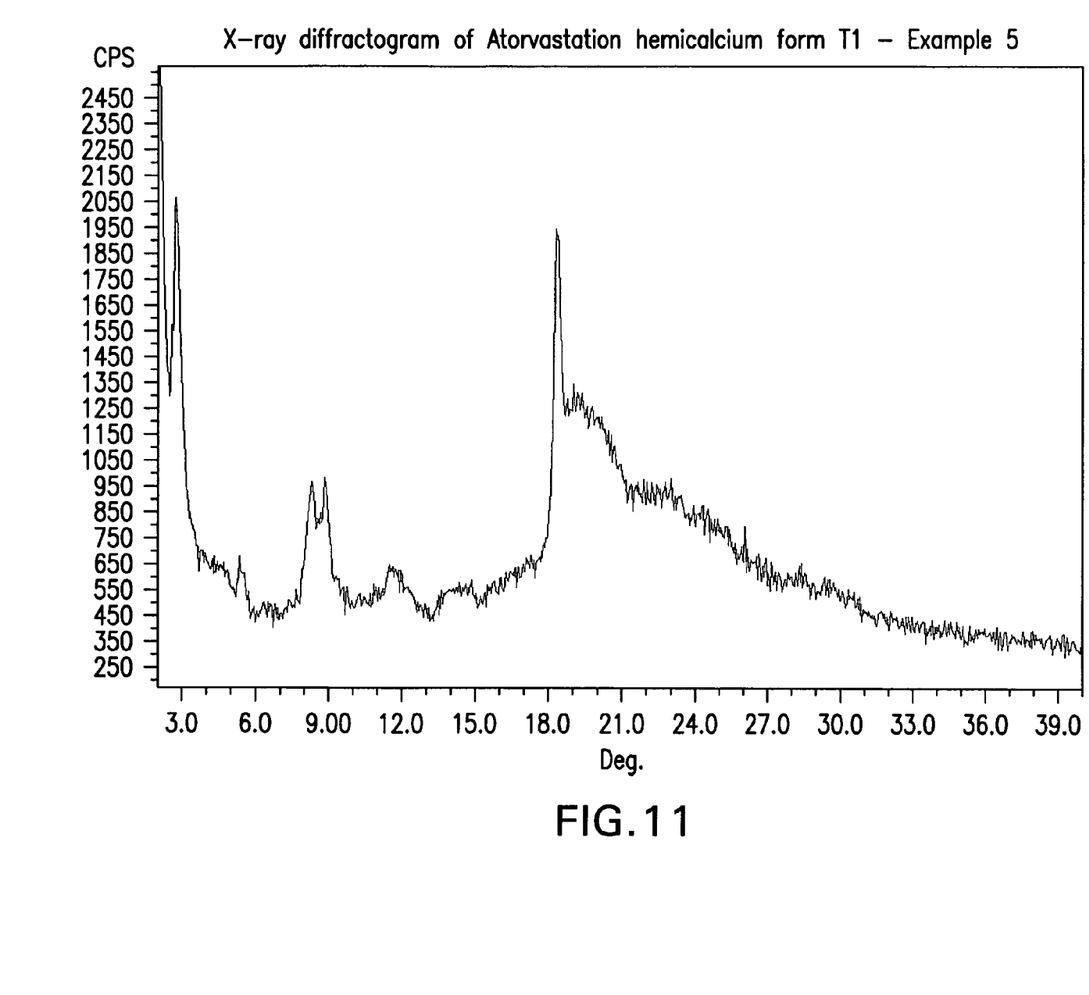
FIG. 11 is an X-ray diffractogram of a sample of Atorvastatin hemicalcium form T1 obtained from Example 5.

This crystalline form is characterized by a powder XRD pattern with most intense peaks at 2.9, 8.25, 8.95 and 18.4±0.25 degrees 2θ. Preferably, the most intense peaks are in the range of 2.7-2.9, 8.0-8.5, 8.7-9.2 and 18.3-18.6 degrees 2θ. It may be further characterized by a powder XRD pattern with peaks at 4.85, 5.7 and 19.9±0.25 degrees 2θ. Preferably, the peaks are in the range of 4.6-5.1, 5.5-5.8 and 19.7-19.9 degrees 2θ. Form T1 may further be characterized by an X-ray powder diffraction patterns substantially as depicted in any one of FIGS. 1-11.

An X-Ray powder diffraction of a crystalline form often consists of a set of peaks that differ in degree of intensity. The term "most intense peaks" refers to the peaks which their height (by means of distance from the baseline) is tallest.

The present invention further provides a process for preparing atorvastatin hemi-calcium Form T1. This process comprises slurrying atorvastatin hemi-calcium Form V in a mixture of ethanol and water. A slurry refers to a heterogeneous mixture.

Preferably, the ethanol comprises about 60% to about 85% by volume of the ethanol-water mixture used for the slurrying process More preferably, the ethanol comprises about 70% to about 75% by volume of the ethanol-water mixture used for the slurrying process.

Preferably, the atorvastatin hemi-calcium Form V is slurried for a period of about 1 minute to about 15 hours. More preferably, Form V is slurried for a period of about 5 minutes to about 30 minutes.

The slurry process is preferably carried out from a temperature of about 20° C. to about 50° C. In one embodiment, the slurry is carried out at room temperature.

The slurry process uses atorvastatin hemi-calcium Form V as a starting material. This form and processes for its preparation are disclosed in International Publication No. WO 01/36384. According to the '384 publication, Form V has a $^{13}C$ NMR signal at about 21.9, 25.9, 118.9, 122.5, 128.7, 161.0 and 167.1 ppm. Form V may be prepared by dissolving atorvastatin calcium in a solvent selected from the group consisting of tetrahydrofuran and hydroxylic solvents to form an atorvastatin calcium salt solution and adding water to the atorvastatin calcium salt solution. Solvents such as ethanol and methanol may be used. Form V may also be prepared by dissolving a metal, ammonium or alkylammonium salt of atorvastatin in a solvent to form an atorvastatin salt solution and contacting the atorvastatin salt solution with a calcium salt. The disclosure of the '384 publication as to preparation and characterization of Form V is herein incorporated by reference.

The obtained crystalline form T1 may be recovered from the ethanol and water mixture by various methods. In one method, the crystalline form is recovered by filtration. The crystalline form may also be dried. Preferably, the crystalline form is dried at a temperature of about 20° C. to about 80° C. In one embodiment, drying is carried out at about 40° C. The drying process may also be carried out at ambient or reduced pressure, such as that below about 100 mmhg. In one embodiment, a fluidized bed dryer is used.

Form T1 may be obtained in various degrees of crystallinity. This degree of crystallinity can affect the intensity and broadness of the powder XRD peaks.

One of ordinary skill of art would appreciate that a composition obtained from a particular process may not be 100% polymorphically pure. Preferably, the crystalline atorvastatin hemi-calcium Form T1 is present in a composition with a polymorphic purity of at least about 50%, more preferably at least about 80%, and most preferably at least about 90% by weight. The level of purity can be determined by methods known in the art, such as powder X-ray diffraction.

The present invention further provides pharmaceutical compositions comprising atorvastatin hemi-calcium Form T1 and at least one pharmaceutically acceptable excipient.

The pharmaceutical compositions of the invention include powders, granulates, aggregates and other solid compositions comprising Form T1 of atorvastatin hemi-calcium. In addition, Form T1 solid formulations that are contemplated by the present invention may further include diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin.

Further excipients that are within the contemplation of the present invention include binders, such as acacia gum, pregelatinized starch, sodium alginate, glucose and other binders used in wet and dry granulation and direct compression tableting processes. Excipients that also may be present in a solid formulation of Form T1 atorvastatin hemi-calcium further include Disintegrants like sodium starch glycolate, crospovidone, low-substituted hydroxypropyl cellulose and others. In addition, excipients may include tableting lubricants like magnesium and calcium stearate and sodium stearyl fumarate; flavorings; sweeteners; preservatives; pharmacy parenteral (including subcutaneous, intramuscular, and intravenous), inhalant and ophthalmic administration. Although the most suitable route in any given case will depend on the nature and severity of the condition being treated, the most preferred route of the present invention is oral. Dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of atorvastatin hemi-calcium whereupon the properties that distinguish the solid forms of atorvastatin hemi-calcium are lost. However, the use of the novel forms to prepare such solutions (e.g. so as to deliver, in addition to atorvastatin, a solvate to said solution in a certain ratio with a solvate) is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The pharmaceutical compositions can contain, for example, about 0.5 mg to about 100 mg, preferably about 2.5 mg to about 80 mg atorvastatin or atorvastatin hemi-calcium Form T1. Preferably, the composition contains about 10, 20, 40 or 80 mg of atorvastatin or atorvastatin hemi-calcium Form T1. The compositions can be administered, for example, once or multiple times per day to a human.

Preferably, the pharmaceutical composition comprising atorvastatin hemi-calcium Form T1 is administered to a human to reduce the level of LDL particle concentration in the blood stream in the human and/or reduce the risk of cardiovascular disease.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Powder X-ray diffraction ("PXRD") analysis was performed using a SCINTAG powder X-ray diffractometer model X'TRA equipped with a solid-state detector. Copper radiation of $\lambda=1.5418$ Å was used. The sample was introduced using a round standard aluminum sample holder with round zero background quartz plate in the bottom.

Example 1

A 2.8 g mixture of ethanol (2 g) and water (0.8 g) was sprayed on dry atorvastatin calcium form V (20 g), the obtained wet material was mixed about 5 minutes at room temperature and dried in a vacuum oven at 40° C. to yield Form T1, having peaks at about 2.9, 4.6, 5.5, 8.3, 9.0, 10.4, 11.8, 17.1 and 18.4 degrees 2-theta.

Example 2

50 ml of 74% ethanol (i.e. 26% water) was added to dry ATV form V (10 g), the obtained slurry mixture was stirred about 30 min at room temperature. After filtration the obtained wet material was dried in a vacuum oven at 40° C. to yield Form T1, having peaks at about 2.9, 4.7, 5.5, 8.1, 8.7 and 18.3 degrees 2-theta.

Example 3

Step 1:
100 ml of 74% ethanol was added to dry ATV form V (20 g), and the obtained slurry mixture was stirred about 120 min at room temperature.
Step 2:
Half of the slurry mixture obtained in step 1 was filtered, and the obtained wet material was dried in a vacuum oven at 40° C. to yield Form T1, having peaks at about 2.9, 5.1, 5.7, 8.3, 9.1 and 18.4 degrees 2-theta.
Step 3:
The remaining half of the slurry mixture (obtained in step 1) was filtrated after 13 hr stirring at room temperature, and the obtained wet material was dried in a vacuum oven at 40° C. to yield Form T1, having peaks at about 2.8, 5.0, 5.7, 8.3, 8.8 and 18.3 degrees 2-theta.

Example 4

Step 1:
150 ml of 74% ethanol was added to dry ATV form V (30 g), the obtained slurry mixture was stirred at room temperature and the following sampling were performed after 10, 20, 30 minutes, respectively.

Step 2:

The first part of the product obtained in Step 1 was filtrated after 10 min stirring at room temperature. The obtained wet material was dried in a vacuum oven at 40° C. to yield Form T1, having peaks at about 2.7, 4.3, 5.1, 7.0, 8.0, 8.7, 11.2, 12.1, 18.4 and 19.9 degrees 2-theta (wet material) and at about 2.8, 5.0, 5.7, 8.3, 9.0, 10.4 and 18.4 degrees 2-theta (dry material).

Step 3:

The second part of the product obtained in Step 1 was filtrated after 20 min stirring at room temperature. The obtained wet material was dried in a vacuum oven at 40° C. to yield Form T1, having peaks at about 2.9, 4.7, 5.7, 8.5, 9.0, 12.0 and 18.5 degrees 2-theta (wet material) and at about 2.9, 5.1, 5.8, 8.5, 9.2, 10.4 and 18.6 degrees 2-theta (dry material).

Step 4:

The third part of the product obtained in Step 1 was filtrated after 30 min stirring at room temperature. The obtained wet material was dried in a vacuum oven at 40° C. to yield Form T1, having peaks at about 2.8, 4.7, 5.7, 8.3, 9.0, 10.5, 11.7 and 18.4 degrees 2-theta (wet material) and at about 2.9, 5.1, 5.7, 8.5, 9.2, 10.4 and 18.5 degrees 2-theta (dry material).

Example 5

150 grams of atorvastatin calcium form V were transferred into a Diosna high shear mixer and the material was mixed for 5 minutes. 21 grams of granulation liquid (made up of 23.8% purified water and 76.2% of 95% ethanol) was poured into the Diosna. The composition of atorvastatin and solvent was mixed for 60 seconds at a mixer speed of 460 rpm and a chopper speed of 1550 rpm. The wet atorvastatin calcium was dried in a Glatt® fluid bed dryer until it reached 2.0% by weight loss on drying (inlet air temp: 45° C.) to yield Form T1, having peaks at about 2.8, 5.4, 8.4, 8.9 and 18.4 degrees 2-theta.

What is claimed is:

1. A crystalline atorvastatin hemi-calcium characterized by a powder XRD pattern comprising most intense peaks at 2.9, 8.25, 8.95 and 18.4±0.25 degrees 2θ.

2. The crystalline atorvastatin hemi-calcium of claim 1, comprising most intense peaks in the range of 2.7-2.9, 8.0-8.5, 8.7-9.2 and 18.3-18.6 degrees 2θ.

3. The crystalline atorvastatin hemi-calcium of claim 1, further characterized by a powder XRD pattern comprising peaks at 4.85, 5.7 and 19.9±0.25 degrees 2θ.

4. The crystalline atorvastatin hemi-calcium of claim 3, characterized by peaks in the range of 4.6-5.1, 5.5-5.8 and 19.7-19.9 degrees 2θ.

5. The crystalline atorvastatin hemi-calcium of claim 1, further characterized by an X-ray powder diffraction pattern substantially as depicted in any one of FIGS. 1-11.

6. The crystalline atorvastatin hemi-calcium of claim 1, wherein the crystalline atorvastatin hemi-calcium is present in a composition of at least about 50% polymorphic purity by weight.

7. The crystalline atorvastatin hemi-calcium of claim 6, wherein the crystalline atorvastatin hemi-calcium is present in a composition of at least about 80% polymorphic purity by weight.

8. The crystalline atorvastatin hemi-calcium of claim 6, wherein the crystalline atorvastatin hemi-calcium is present in a composition of at least about 90% polymorphic purity by weight.

9. A process for preparing the crystalline atorvastatin hemi-calcium of claim 1 comprising: slurrying atorvastatin hemi-calcium Form V in a mixture of ethanol and water to obtain the crystalline atorvastatin hemi-calcium.

10. The process of claim 9, further comprising recovering the atorvastatin hemi-calcium.

11. The process claim 9 wherein the atorvastatin hemi-calcium Form V is slurried in the mixture of ethanol and water for a period of at least about 5 minutes.

12. The process of claim 11 wherein the ethanol comprises at least about 60% of the mixture.

13. The process of claim 11 wherein the ethanol comprises at least about 70% of the mixture.

14. The process of claim 11, further comprising drying the crystalline atorvastatin hemi-calcium.

15. The process of claim 14 wherein the crystalline atorvastatin hemi-calcium is dried at a temperature of 20° C. to about 80° C.

* * * * *